United States Patent
Babaev

(12) 
(10) Patent No.: US 6,569,099 B1
(45) Date of Patent: May 27, 2003

(54) ULTRASONIC METHOD AND DEVICE FOR WOUND TREATMENT

(76) Inventor: Eilaz Babaev, 5564 Bimini Dr., Minnetonka, MN (US) 55343

( * ) Notice: Subject to any disclaimer, the term of this patent is extended or adjusted under 35 U.S.C. 154(b) by 279 days.

(21) Appl. No.: 09/669,312

(22) Filed: Jan. 12, 2001

(51) Int. Cl.$^7$ .................................................. A61B 8/00
(52) U.S. Cl. ............................. 600/439; 601/2; 601/3; 600/437; 604/22
(58) Field of Search .................... 601/2, 3; 600/437, 600/439; 604/22, 24

(56) References Cited

U.S. PATENT DOCUMENTS

| | | |
|---|---|---|
| 3,561,444 A | 2/1971 | Boucher |
| 4,271,705 A | 6/1981 | Crostack |
| 4,301,093 A | 11/1981 | Eck |
| 4,309,989 A | 1/1982 | Fahim |
| 4,319,155 A | 3/1982 | Nakai et al. |
| 4,334,531 A | 6/1982 | Reichl et al. |
| 4,582,654 A | 4/1986 | Karnicky et al. |
| 4,726,525 A | 2/1988 | Yonekawa et al. |
| 4,793,339 A | 12/1988 | Matsumoto et al. |
| 4,877,989 A | 10/1989 | Drews et al. |
| 5,134,993 A | 8/1992 | van der Linden et al. |
| 5,315,998 A | 5/1994 | Tachibana et al. |
| 5,515,841 A | 5/1996 | Robertson et al. |
| 5,515,842 A | 5/1996 | Ramseyer et al. |
| 5,551,416 A | 9/1996 | Stimpson et al. |
| 5,785,972 A | 7/1998 | Tyler |
| 6,041,253 A | 3/2000 | Kost et al. |
| 6,104,952 A | 8/2000 | Tu et al. |
| RE36,939 E | 10/2000 | Tachibana et al. |
| 6,190,315 B1 | 2/2001 | Kost et al. |
| 6,234,990 B1 | 5/2001 | Rowe et al. |
| 6,251,099 B1 | 6/2001 | Kollias et al. |
| 6,296,630 B1 | 10/2001 | Altman et al. |

FOREIGN PATENT DOCUMENTS

| | | |
|---|---|---|
| GB | 2 099 710 A | 12/1982 |
| GB | 2 101 500 A | 1/1983 |

*Primary Examiner*—Teresa Walberg
*Assistant Examiner*—Shawntina Fuqua
(74) *Attorney, Agent, or Firm*—Carter, DeLuca, Farrell & Schmidt, LLP

(57) ABSTRACT

The method and device of the present invention for wound treatment includes a transducer to produce waves, preferably ultrasonic waves. The transducer has tip with the distal end (radiation surface). A liquid is directed to the radiation surface wherein an directed atomized particle spray of the liquid is created upon contact of the liquid with the radiation surface. The spray directed to the wound from at least 0.1 inches transmits wave trough particles and has an irrigation, mechanical cleansing, liquid energizing and bactericide effect.

20 Claims, 4 Drawing Sheets

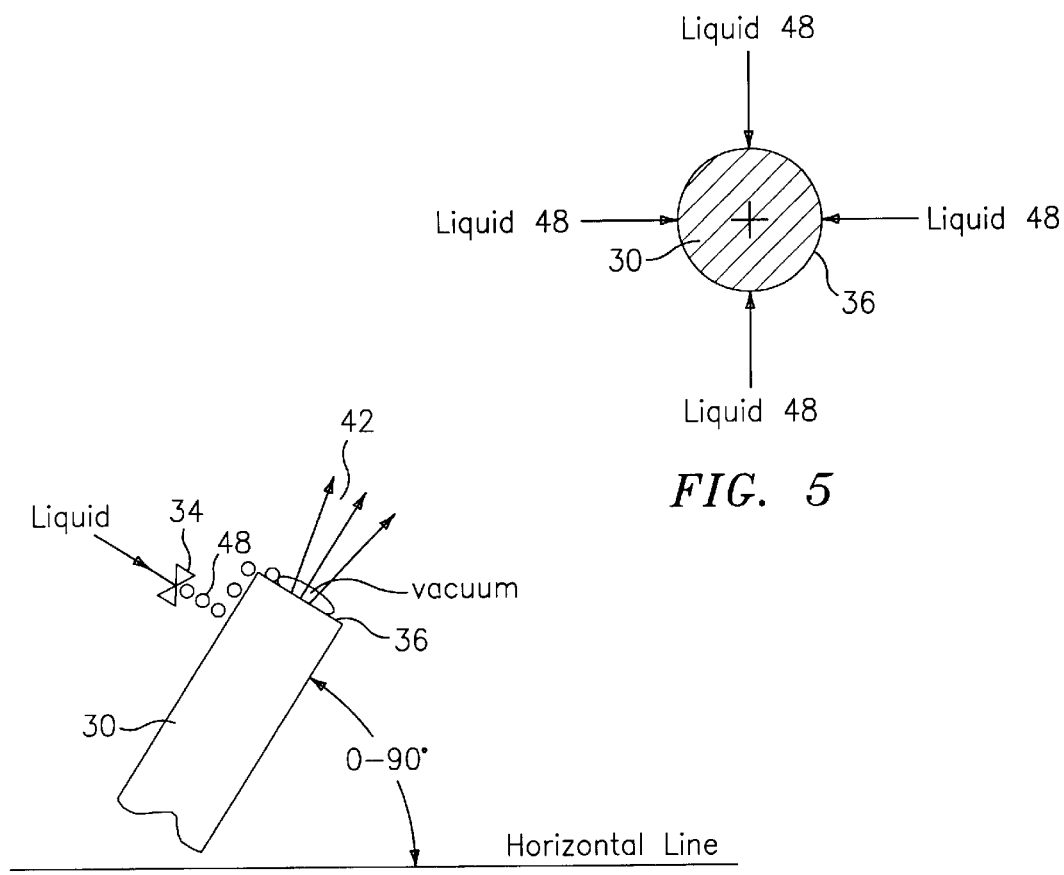
FIG. 5
FIG. 6
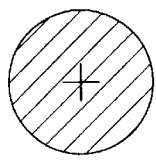
FIG. 7a
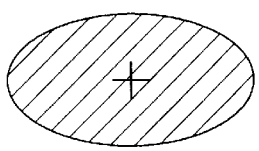
FIG. 7b
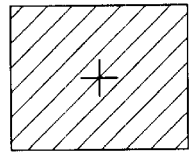
FIG. 7c
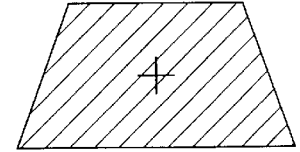
FIG. 7d
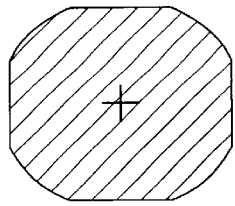
FIG. 7e
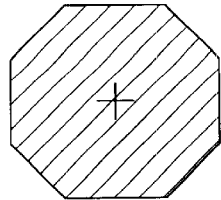
FIG. 7f
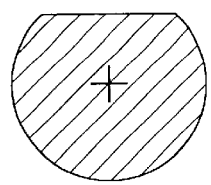
FIG. 7g

ULTRASONIC METHOD AND DEVICE FOR WOUND TREATMENT

FIELD OF THE INVENTION

The present invention relates to methods of using ultrasonic waves in wound treatment. More particularly, the present invention relates to a method of spraying a wound surface using ultrasonic waves for delivering drugs, killing bacteria, cleansing a surface and stimulating healthy tissue cells.

BACKGROUND OF THE INVENTION

Ultrasonic waves has been widely used in medical applications, including both diagnostics and therapy as well as many industrial applications. One diagnostic use of ultrasound waves includes using ultrasonic waves to detect underlying structures in an object or a human tissue. In this procedure, an ultrasonic transducer is placed in contact with the object or tissue via a coupling medium and high frequency (1–10 MHz) ultrasonic waves are directed into the tissue. Upon contact with various underlying structures, the waves are reflected back to a receiver adjacent the transducer. By comparison of the signals of the ultrasonic wave as sent with the reflected ultrasonic wave as received, an image of the underlying structure can be produced. This technique is particularly useful for identifying boundaries between components of tissue and can be used to detect irregular masses, tumors, and the like.

Two therapeutic medical uses of ultrasound waves include aerosol mist production and contact physiotherapy. Aerosol mist production makes use of a nebulizer or inhaler to produce an aerosol mist for creating a humid environment and delivering drugs to the lungs. Ultrasonic nebulizers operate by the passage of ultrasound waves of sufficient intensity through a liquid, the waves being directed at an air-liquid interface of the liquid at a point underneath or within the liquid. Liquid particles are ejected from the surface of the liquid into the surrounding air following the disintegration of capillary waves produced by the ultrasound. This technique can produce a very fine dense fog or mist. Aerosol mists produced by ultrasound are preferred over aerosol mists produced by other methods because a smaller particle size of aerosol can be obtained with the ultrasonic waves. One of the major shortcoming of inhalers and nebulizers is that the aerosol mist cannot be directed to a target area without an air stream, which decreases the efficiency of ultrasound.

Ultrasonic sprayers such as those sold by Sonic and Materials Inc., Misonix Inc., Sono-Tek Inc. (see, for example, U.S. Pat. Nos. 4,153,201, 4,655,393, and 5,516,043) operate by passing liquid through a central orifice of an ultrasound instrument-tip. Major disadvantages of these sprayers include non-uniform particle size, heating of liquid flow, and less efficiency of ultrasound waves because of demolished end (radiation) surface of tip.

Contact physiotherapy applies ultrasonic waves directly to tissue in an attempt to produce a physical change in the tissue. In conventional ultrasound physiotherapy, an ultrasonic wave contacts the tissue via a coupling medium. Ultrasonic waves produced by the transducer travel through the coupling medium and into the tissue. The coupling medium is typically a bath of liquid, a jelly applied to the surface to be treated, or a water-filled balloon. Conventional techniques provide ultrasonic waves having an intensity of about 0.25 w/cm$^2$ to 3 w/cm$^2$ at a frequency of about 0.8 to 3 Megahertz. The treatment is applied to a skin surface for from about 1 to 30 minutes, two or three times a week. The coupling medium can provide a cooling effect which dissipates some of the energy produced by the ultrasonic transducer.

More importantly, a coupling medium or direct contact between the tissue and ultrasonic transducer is necessary to transmit the ultrasonic waves from the to the skin surface because ambient air is a relatively poor medium the propagation of ultrasonic waves.

Several beneficial effects have been reported from contact ultrasound physiotherapy, such as, for example, the following: local improvement of the blood circulation, heating of the tissue, accelerated enzyme activity, muscle relaxation, pain reduction, and enhancement of natural healing processes. Despite these beneficial effects, current techniques of medical physiotherapy using ultrasonic waves are limited by the necessity of providing a direct contact interface between the ultrasonic transducer and the tissue to maintain an effective transmission of the ultrasonic waves from the transducer to the tissue.

The necessity of direct contact with or without a coupling medium makes current methods undesirable. Some tissue conditions may be accessible to contact ultrasound devices but would be impractical for contact ultrasound treatment. For example, fresh or open wounds resulting from trauma, burns, surgical interventions are not suitable for direct contact ultrasound treatment because of the structural nature of the open wound and the painful condition associated with those wounds. Moreover, conventional contact ultrasound may have a destructive effect on these types of open wounds due to the close proximity of an oscillating tip of an ultrasonic transducer relative to the already damaged tissue surface.

OBJECT OF THE INVENTION

It is an object of the invention to provide an improved method and device for treating wounds.

It is also an object of this invention to provide a method and device for treating wounds using ultrasonic waves.

It is a further object of the invention to provide a method and device for delivering drugs, killing bacteria, cleansing a surface, or stimulating healthy tissue cell growth.

It is a yet further object of the invention to treat a wound by spraying the surface of the wound with aerosol mist produced by ultrasonic waves.

These and other objects of the invention will become more apparent from the discussion below.

SUMMARY OF THE INVENTION

The present invention relates to a method and device for spraying a wound surface to deliver drugs, kill bacteria, or cleanse a surface by non-contact application of an ultrasound transducer tip. The method applies ultrasonic waves to the wound without requiring direct or indirect (via a traditional coupling medium) contact between the ultrasonic wave transducer and the wound to be sprayed.

The method of the invention comprises producing a directed spray of liquid particles produced by contact of the liquid with a free end surface of an ultrasonic transducer. The ultrasonic waves cause the spray to project outwardly from the distal end surface of the ultrasonic transducer, and the particle spray is directed onto the wound. The particles of the spray provide a medium for propagation of the ultrasonic waves emanating from the distal end surface.

According to the method of the present invention directed particle spray created by low frequency ultrasound waves onto a wound, delivers drug, kills bacteria on that wound, increases blood flow, and removes dirt and other contaminants from that surface (mechanical cleansing).

This method of drug delivery is particularly advantageous on tissues for which local topical application of a drug is desirable but contact with the tissue is to be avoided. Furthermore, the low frequency ultrasound waves used in the method energize the drug and cause penetration of the drug below the surface of the tissue. Finally, the bacteria killing method is effective when applied to the surface whether the liquid sprayed is drug (an antiseptic or antibiotic), oil, saline, distilled water, etc.

BRIEF DESCRIPTION OF THE DRAWINGS

FIG. 5 represents a cross-sectional view of the distal end of the ultrasonic transducer when liquid is delivered to the side or radiation surface of the transducer tip from 360° by perimeter as a top, side, bottom, etc;

FIG. 6 is a variation of the detail of FIG. 4b which illustrates the spraying effect by changing the angle between the ultrasound instrument and horizontal line from 0° to 90°;

FIGS. 7a to 7g are each a cross-sectional view of a useful ultrasound tip;

DETAILED DESCRIPTION OF THE INVENTION

Figure 1:
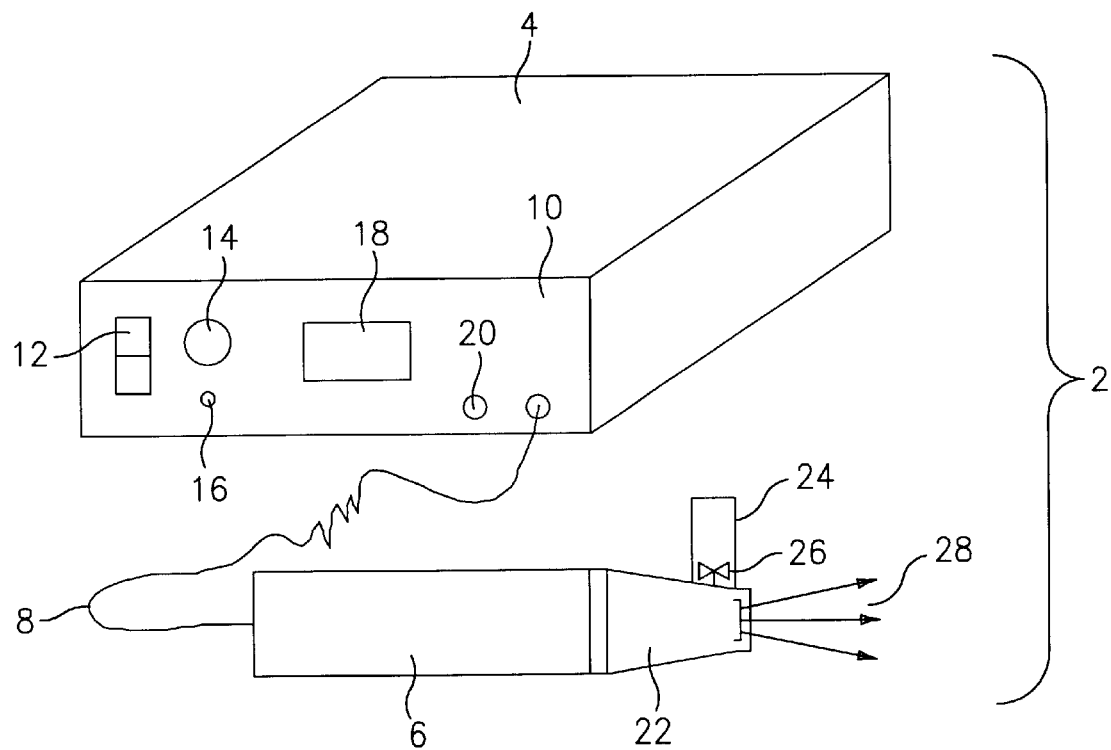
FIG. 1 is a perspective view of an ultrasonic wound treatment system for use according to the present invention.
Figure 2:
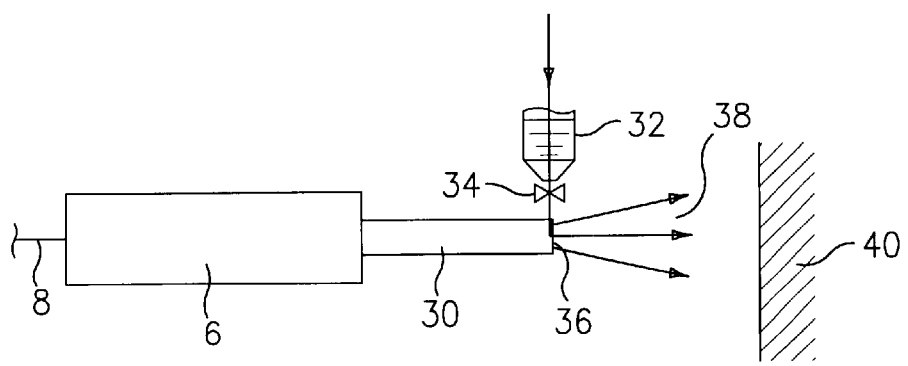
FIG. 2 is a lateral schematic view of an ultrasonic sprayer useful according to the present invention.
Figure 3:
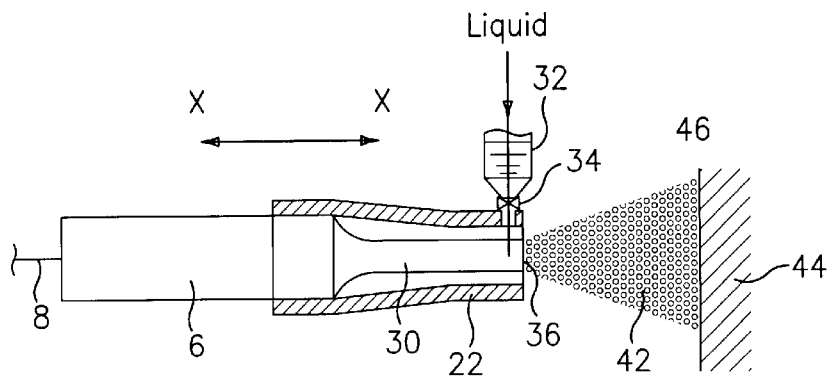
FIG. 3 is a partly cross-sectional view of an ultrasonic sprayer in use according to the present invention.
Figure 4A:
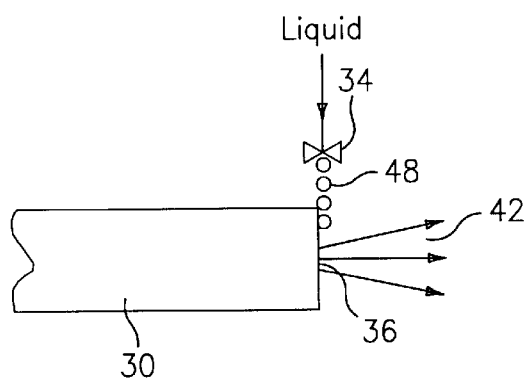
FIGS. 4a and 4b are each a detail of the sprayer shown in FIG. 3 for spraying liquid from a radiation surface (FIG. 4a) or from a side (radial) surface, based on the Babaev effect (FIG. 4b)
Figure 4B:
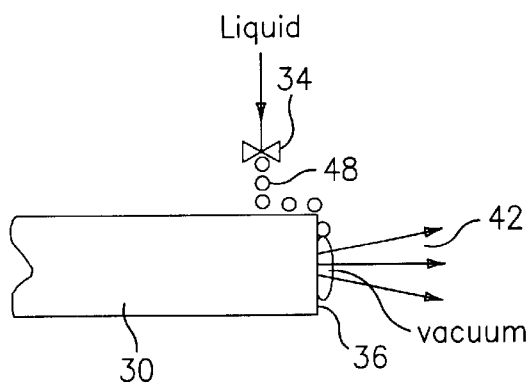
Figure 8A:
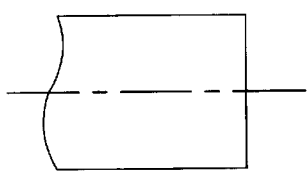
FIGS. 8a to 8i are each an enlarged view of a different modification of a tip end shape of the ultrasonic sprayer used according to the present invention.
Figure 8B:
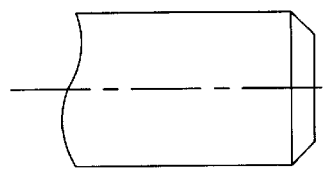
Figure 8C:
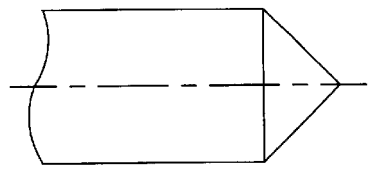
Figure 8D:
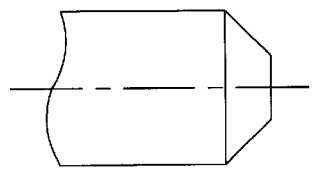
Figure 8E:
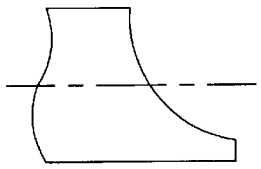
Figure 8F:
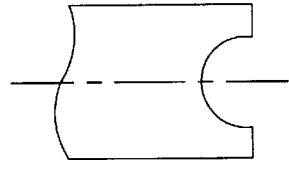
Figure 8G:
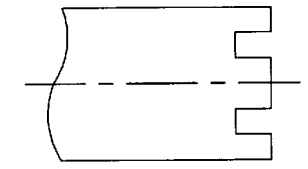
Figure 8H:
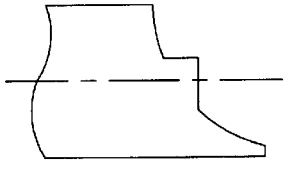
Figure 8I:
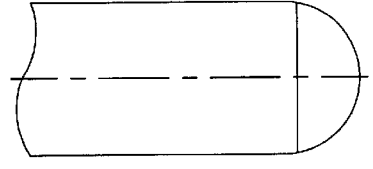

The device of the invention that produces a spray is characterized by means for first delivering the liquid to a lateral surface of an ultrasonic transducer tip adjacent to a free end surface such that the liquid is pulled to the free end surface by a vacuum (negative pressure) created by the ultrasound waves on the free end surface of the transducer tip. This effect can be achieved while the angle between the ultrasound instrument and the horizontal is modified up to 90°. (This acoustical effect of delivering liquid from radial side of a tip to the free end was discovered by the inventor of this invention and is called the "Babaev effect".) This effect occurs when liquid is delivered to the radial surface of a transducer tip from 360° by perimeter as a top, side, bottom, etc.

For the above purpose the device must have a so-called nozzle from steel (non-disposable) or plastic (disposable) with a different design of valve. The nozzle allows delivery of liquid to the lateral surface of the transducer tip or directly to the distal side (radiation surface) of the ultrasound transducer to act as a sprayer or atomizer.

One of the major advantages of the invention is the uniformity of the spray particles generated. Because liquid is sprayed from a solid radiation surface, there is substantial uniformity of particle size, about 90% or greater, preferably from about 90 to 96%. It is provided that the distal radiation surface is driven with constant frequency to create the spray. It is also provided that the driving frequency can be modulated during treatment and that the distal radiation surface is driven with a sinusoidal, rectangular, trapezoidal or triangular wave form.

The step of producing the spray can further include operating the transducer to produce ultrasonic waves having a frequency of from about 18 kHz to 10,000 MHz. Frequencies below 18 kHz, i.e., from about 1 to 18 kHz, can be used as well; however, this lower range is less desirable because this range of sound wave can be uncomfortable to the patient and operator (without ear protection or the like). Frequencies in the range of from about 30 to 100 kHz are preferred, and frequencies of about 40 kHz are most preferred.

The separation distance between the free end surface of the transducer and the surface or object to be sprayed should be a "non-contact" distance of at least 0.1 in. (2.5 mm). Preferably the separation distance is from about 0.1 in. (2.5 mm) to 20 in. (51 cm), more preferably from about 0.1 in. (2.5 mm) to 5 in. (12.7 cm). The liquid to be sprayed can be any appropriate carrier such as water (regular or distilled), saline solution, or oil to be applied to tissue, such as a vegetable, peanut, or canola oil, optionally with a soluble pharmaceutical (e.g., an antibiotic), antiseptic, conditioner, surfactant, emollient, or other active ingredient. The pharmaceutical or the like is preferably present in a concentration sufficiently low to be soluble but high enough to be effective for the intended purpose.

It is within the scope of the invention that the liquid to be sprayed could comprise a mixture of two or more immiscible liquids or a heterogeneous mixture of a solution and small particles. It is also within the scope of the invention that the spray could comprise particles, such as powder.

The spray produced according to the invention is directed to the object, surface, or tissue to be sprayed for the time and frequency required to accomplish a particular purpose or treatment. It is believed that a minimum length of spray of at least one second will be required; however, the length or duration of the spray could be from about one second to as much as a minute or more, even 30 minutes. Numerous factors or circumstances, such as, for example, the area to be sprayed (e.g., the size of a wound), the volume rate of spray produced, the concentration of active ingredient, etc., will impact upon the duration and/or frequency of the spraying. Spraying could be required from one or more times daily to as little as two or three times a week or month.

According to the invention ultrasonic waves are applied to a wound without establishing contact, directly or indirectly, between the ultrasonic transducer and the wound. For example, surfaces of the human body especially suited for treatment with the method of the present invention include infected and inflammatory situations in open wounds, including trauma or gun shut wounds, fire and chemical burns.

In addition, the method of the present invention is particularly suited to directing a spray into orifices or other body crevices that are difficult to access.

Wound treatment according to the invention has several advantages. First, this method topically applies medicines such as liquid antibiotics to the wound surface without the need to contact infected, inflamed or painful tissue with an instrument. And second, a significant bactericidal effect occurs when a wound surface is sprayed using the method of the present invention.

Moreover, aside from the bactericidal effect and advantages of non-contact treatment, using the method of the present invention gave a significant reduction in volume used of liquid medicine used as compared with traditional methods for wound treatment. Similarly, this allows for precise dosage of the sprayed liquid to permit a user, such as a physician, to administer the desired volume of liquid at a desired rate and duration.

It has been found that the method of the present invention decreases healing times for inflammatory and purulent infected wounds that is from about 1.5 to 3 times faster than traditional methods. This effect results from a bactericidal, blood flow increasing and mechanical cleansing effect of the atomized spray particles, which have ultrasound energy due to the ultrasonic waves. The spray mechanically scrubs the surface of tissue to remove dirt, dead tissue, and purulent buildup on the tissue surface. The mentioned healing effect also results of energized and highly activated antibiotics, drug penetration into the tissue surface up to 0.5 mm in depth under influence of ultrasound waves.

Additionally, a combination of the low frequency ultrasonic waves and the sonicated medicines (highly activated by ultrasonic energy) destroy the surface bacteria to result in a higher disinfecting property of sonicated liquids as compared to ordinarily applied liquids. The spray of the present method also stimulates healthy cell growth to aid in granulization and epithelization of the healing tissue.

Other applications of the invention can be directed to non-medical uses such as cleansing, sterilizing and coating surfaces of objects and food.

The method of the present invention offers an approach that may re-establish use of some traditional antibiotics and establish a method fighting bacteria without antibiotics when necessary. The effect of the method of the present invention in highly activating antibiotics may allow some traditional antibiotics to overcome bacteria which have become resistant to that antibiotic. Moreover, independent of the sonication effect of the antibiotics, the low frequency ultrasonic waves applied in the method of the present invention physically destroy bacteria. The combination of the highly activated antibiotics and of the low frequency ultrasonic waves in the method of the present invention produce a strong bactericidal effect not found in mere topically application or orally ingested antibiotics. This combined effect has been shown to significantly increase the healing of purulent infected wounds.

The present method also provides a system of non-contact drug delivery without use of a compression sprayer system. This simplifies the design of a non-contact drug delivery sprayer and reduces the weight of the sprayer. More importantly, not using compression to propel the atomized particles preserves the ultrasound energy carried by the spray particles.

This ultrasound energy has been proven to destroy bacteria by action of the ultrasonic waves and by highly activated liquid medicines applied to the tissue.

The method of the present invection provides a method of compressionless non-contact drug delivery.

The invention can perhaps be better appreciated by making reference to the drawings. In FIG. 1, an ultrasonic treatment system 2 comprises an ultrasound wave generator 4, connected to an ultrasound transducer 6 by a cable 8. The wave generator 4, which is conventional, may have a front panel 10 with a power button 12, a timer 14, a control button 16, one or more displays 18, and one or more jacks 20, for example, for a footswitch (not shown). A nozzle 22 having a liquid reservoir 24 with a valve 26 is attached to the distal portion of transducer 6. Arrows 28 represent the direction of spray produced.

FIG. 2 is a simplified representation of an ultrasonic device and spray according to the invention. Transducer 6 has a distal transducer tip or horn 30. Liquid from a liquid reservoir 32 flows through a valve 34 to a position adjacent the distal radiation surface 36 of a horn 30. Transducer 6 is attached to an ultrasound source via cable 8. A liquid mist is directed in the direction of arrows 38 to target tissue or surface 40.

FIG. 3 is an enlarged, partly cross-sectional view of a section of FIG. 1 illustrating a spray created by the device according to the method of the present invention. This device is a modification and implementation of a device disclosed in U.S. Pat. No. 5,076,266, which is incorporated herein by reference. As can be seen in more detail in FIG. 3, nozzle 22 surrounds ultrasound horn 30. Also, liquid reservoir 32 has a valve 34 positioned between reservoir 32 and the distal surface 36 of ultrasonic horn 30. A conical spray pattern of liquid droplets 42 is directed at a surface or tissue 44 of a target. This configuration is effective to spray liquid onto a surface and to deliver ultrasonic waves to that surface, such as, for example, the surface of a wound.

Valve 34 allows liquid to flow to distal tip 36 as drops or continuous flow through gap 46. Valve 34 may be located anywhere, including between reservoir 32 and horn 30. Mechanical movement of the horn 30 in the direction x—x causes liquid to flow to the distal end or radial surface 36.

FIG. 4*a* is a view of the ultrasonic sprayer as used in a method of the present invention for spraying liquid 48 directed to distal end (radiation surface) 36.

FIG. 4*b* is a view of the basic spraying method from side (radial) surface of the tip based on the Babaev effect. In this case liquid or drug directed to the radial surface 36 of ultrasound horn 30 becomes sonicated (ultrasonically energized), after being pulled forward by negative pressure (vacuum) created by ultrasound waves and sprays.

As shown in FIG. 5, liquid is delivered to the side or radiation surface 36 of transducer horn 30 from 360° along its perimeter as a top, side, bottom, etc.

In the embodiment of the invention shown in FIG. 6, a partial section of transducer horn 30 is elevated from the horizontal up to 90°. Due to the Babaev effect, liquid 48 still travels to radiation surface 36.

The ultrasound tip or horn can can have a regular or irregular lateral cross-section, including circular, oval, elliptical, rectangular, trapezoidal, or a combination thereof. See, for example, FIGS. 7*a* to 7*g*, which are each a view of a cross-section of a ultrasound tip or horn. Also, the distal end shape of the ultrasound tip or horn longitudinal cross-section may vary and may be rectangular, elliptical, oval, spherical, conical, curved, stepped, with chamfer, etc. See, for example, FIGS. 8*a* to 8*i*, which are each an enlarged view in section of a different modification of a tip of the sprayer as used in the method of the present invention. The preferred shape is rectangular, because of radiation bims from ultrasound tip surface fully directed to the target (wound). With the spheric, elliptic and oval (FIG. 8*e*) form of shape end radiation beams are focused at focal point. With other form of shape end, radiation beams are getting spreaded reaching target partly.

Radial side surface of distal end of the tip may have slot (groove) or thread for liquid to be directed to the radiation surface (FIGS. 9*a* to 9*c*).

Figure 9A:
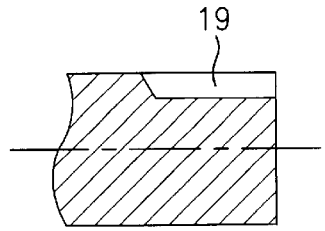
FIGS. 9a, 9b, and 9c represent cross-sectional, distal, and lateral views of the top of an ultrasonic sprayer having a slot, groove, or thread.
Figure 9B:
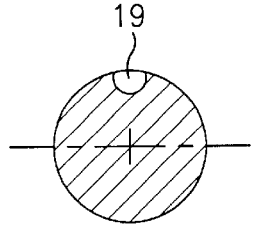
Figure 9C:
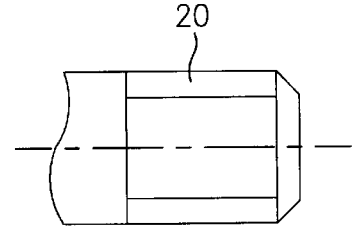

FIGS. 9a to 9c are each a view of radial side surface of distal end of the tip which has a slot (groove) 19 or thread 20 for liquid to be directed to the radiation surface.

The preceding specific embodiments are illustrative of the practice of the invention. It is to be understood, however, that other expedients known to those skilled in the art or disclosed herein, may be employed without departing from the spirit of the invention or the scope of the appended claims.

What is claimed is:

1. A method for treating a wound comprising the steps of:
   providing a transducer having a distal radiation surface arranged a distance from the surface of the wound for emitting ultrasonic energy;
   introducing at least one of a liquid and a powder to the distal radiation surface to produce a spray; and
   delivering the emitted ultrasonic energy to the wound through the spray, wherein the ultrasonic energy penetrates the wound tissue to a beneficial depth to provide a bactericidal and a therapeutic effect for decreasing the healing time for the wound.

2. The method according to claim 1, wherein the transducer operates at a frequency from 18 kHz to 10,000 MHz.

3. The method according to claim 1, wherein the transducer operates at a frequency from 35 kHz to 45 kHz.

4. The method according to claim 1, wherein the distal radiation surface is positioned from 0.1 to 20 inches from the surface of the wound.

5. The method according to claim 1, wherein the liquid includes one or more components selected from the group consisting of antibiotics, antiseptics, saline solutions, oils, and water.

6. The method according to claim 1, wherein the delivering step includes the step of delivering the emitted ultrasonic energy for a predetermined time for achieving the bactericidal and therapeutic effects, and further comprising the step of repeating the treatment method until the wound is healed.

7. The method according to claim 1, wherein the transducer is driven by constant or modulated frequency and wherein the driving wave form of the transducer is selected from the group consisting of sinusoidal, rectangular, trapezoidal and triangular wave forms.

8. The method according to claim 1, wherein the therapeutic effect is selected from the group consisting of increasing blood flow to the wound, mechanically cleansing the wound, stimulating cell growth, providing at least one medicament to the wound, and penetrating at least one medicament through the surface of the wound.

9. An apparatus for treating a wound comprising:

means for generating ultrasonic energy positioned at a non-contact distance from the surface of the wound; and means for introducing at least one of a liquid and a powder to at least one propagation path of the generated ultrasonic energy to produce a spray, wherein the generated ultrasonic energy is delivered to the wound through the spray, and wherein the ultrasonic energy penetrates the wound tissue to a beneficial depth to provide a bactericidal and a therapeutic effect for decreasing the healing time for the wound.

10. The apparatus according to claim 9, wherein the means for generating ultrasonic energy generates ultrasonic energy having a frequency from 18 kHz to 10,000 MHz.

11. The apparatus according to claim 9, wherein the means for generating ultrasonic energy generates ultrasonic energy having a frequency from 35 kHz to 45 kHz.

12. The apparatus according to claim 9, wherein the means for generating ultrasonic energy are configured for being positioned from 0.1 to 20 inches from the surface of the wound.

13. The apparatus according to claim 9, wherein the liquid includes one or more components selected from the group consisting of antibiotics, antiseptics, saline solutions, oils, and water.

14. The apparatus according to claim 9, wherein the generated ultrasonic energy is delivered to the wound for a predetermined period of time for achieving the bactericidal and therapeutic effects.

15. The apparatus according to claim 9, wherein the therapeutic effect is selected from the group consisting of increasing blood flow to the wound, mechanically cleansing the wound, stimulating cell growth, providing at least one medicament to the wound, and penetrating at least one medicament through the surface of the wound.

16. A method for treating a wound comprising the steps of:

generating ultrasonic energy at a distance from the surface of the wound, such that the generated ultrasonic energy propagates through a gaseous medium;

introducing at least one of a liquid and a powder in at least one propagation path of the generated ultrasonic energy to produce a spray; and delivering the generated ultrasonic energy to the wound through the spray, wherein the ultrasonic energy penetrates the wound tissue to a beneficial depth to provide a bactericidal and a therapeutic effect for decreasing the healing time for the wound.

17. The method according to claim 16, wherein the generated ultrasonic energy has a frequency from 18 kHz to 10,000 MHz.

18. The method according to claim 16, wherein the generated ultrasonic energy has a frequency from 35 kHz to 45 kHz.

19. The method according to claim 16, wherein the liquid includes one or more components selected from the group consisting of antibiotics, antiseptics, saline solutions, oils, and water.

20. The method according to claim 16, wherein the therapeutic effect is selected from the group consisting of increasing blood flow to the wound, mechanically cleansing the wound, stimulating cell growth, providing at least one medicament to the wound, and penetrating at least one medicament through the surface of the wound.

* * * * *

UNITED STATES PATENT AND TRADEMARK OFFICE
CERTIFICATE OF CORRECTION

PATENT NO.     : 6,569,099 B1
DATED          : May 27, 2003
INVENTOR(S)    : Eilaz Babaev It is certified that error appears in the above-identified patent and that said Letters Patent is hereby corrected as shown below:

<u>Title page,</u>
Item [22], Filed, "January 12, 2001" should be -- September 25, 2000 --

Signed and Sealed this

Twenty-third Day of September, 2003

JAMES E. ROGAN
*Director of the United States Patent and Trademark Office*

UNITED STATES PATENT AND TRADEMARK OFFICE
CERTIFICATE OF CORRECTION

PATENT NO.        : 6,569,099 B1
APPLICATION NO.   : 09/669312
DATED             : May 27, 2003
INVENTOR(S)       : Eilaz Babaev It is certified that error appears in the above-identified patent and that said Letters Patent is hereby corrected as shown below:

On the title page item [56], should read

U.S. PATENT DOCUMENTS

| Document Number | Date | Name |
|---|---|---|
| 3,275,059 | 09/27/66 | McCullough |
| 3,392,916 | 07/16/68 | Engstrom et al. |
| 3,860,173 | 01/14/75 | Sata |
| 4,052,004 | 10/04/77 | Martin et al. |
| 4,085,893 | 04/25/78 | Durley, III |
| 4,153,201 | 05/08/79 | Berger et al. |
| 4,251,031 | 02/17/81 | Martin et al. |
| 4,294,407 | 10/13/81 | Reichl et al. |
| 4,301,968 | 11/24/81 | Berger et al. |
| 4,352,459 | 10/82 | Berger et al. |
| 4,428,531 | 01/31/84 | Martin |
| 4,466,571 | 08/21/84 | Muhlbauer |
| 4,530,360 | 07/23/85 | Duarte |
| 4,541,564 | 09/17/85 | Berger et al. |
| 4,619,400 | 10/28/86 | Van Der Burgt |
| 4,642,581 | 02/10/87 | Erickson |
| 4,655,393 | 04/07/87 | Berger |

UNITED STATES PATENT AND TRADEMARK OFFICE
CERTIFICATE OF CORRECTION

PATENT NO.        : 6,569,099 B1
APPLICATION NO. : 09/669312
DATED             : May 27, 2003
INVENTOR(S)      : Eilaz Babaev It is certified that error appears in the above-identified patent and that said Letters Patent is hereby corrected as shown below:

On the title page item [56], should read

FOREIGN PATENT DOCUMENTS

| Document Number | Date | Country |
|---|---|---|
| 0 156 4009 A2 | 18/02/85 | EPO |
| 0 437 155 B1 | 20/02/90 | EPO |

OTHER DOCUMENTS

Journal of Burn Care & Rehabilitation; Volume 21, Number 4; July/August 2000 pgs. 333-338

Design and Application of Low-Frequency Ultrasound and its Combination With Laser Radiation in Surgery and Therapy - Critical Reviews in Biomedical Engineering; 2001; pgs. 502-519

UNITED STATES PATENT AND TRADEMARK OFFICE
CERTIFICATE OF CORRECTION

PATENT NO.       : 6,569,099 B1
APPLICATION NO.  : 09/669312
DATED            : May 27, 2003
INVENTOR(S)      : Eilaz Babaev It is certified that error appears in the above-identified patent and that said Letters Patent is hereby corrected as shown below:

On the title page item [56], should read

U.S. PATENT DOCUMENTS

| Document Number | Date | Name |
|---|---|---|
| 4,659,014 | 04/21/87 | Soth et al. |
| 4,679,551 | 07/14/87 | Anthony |
| 4,726,523 | 02/23/88 | Kokubo et al. |
| 4,726,525 | 02/23/88 | Yonekawa et al. |
| 4,733,820 | 03/29/88 | Endo et al. |
| 4,756,478 | 07/12/88 | Endo et al. |
| 4,783,003 | 11/08/88 | Hirabayashi et al. |
| 4,790,479 | 12/13/88 | Matsumoto et al. |
| 4,850,534 | 07/25/89 | Takahashi et al. |
| 4,905,671 | 03/06/90 | Senge et al. |
| 4,930,700 | 06/05/90 | McKown |
| 4,941,618 | 07/17/90 | Hildebrand et al. |
| 4,961,885 | 10/09/90 | Avrahami et al. |
| 5,002,059 | 03/26/91 | Crowley et al. |
| 5,040,537 | 08/20/91 | Katakura |
| 5,063,922 | 11/12/91 | Hakkinen |
| 5,076,266 | 12/31/91 | Babaev |

UNITED STATES PATENT AND TRADEMARK OFFICE
CERTIFICATE OF CORRECTION

PATENT NO. : 6,569,099 B1
APPLICATION NO. : 09/669312
DATED : May 27, 2003
INVENTOR(S) : Eilaz Babaev It is certified that error appears in the above-identified patent and that said Letters Patent is hereby corrected as shown below:

On the title page item [56], should read

FOREIGN PATENT DOCUMENTS

| Document Number | Date | Country |
|---|---|---|
| 0 657 226 B1 | 11/28/94 | EPO |
| JP2000237275A2 | 09/05/00 | Japan |

UNITED STATES PATENT AND TRADEMARK OFFICE
CERTIFICATE OF CORRECTION

PATENT NO. : 6,569,099 B1
APPLICATION NO. : 09/669312
DATED : May 27, 2003
INVENTOR(S) : Eilaz Babaev It is certified that error appears in the above-identified patent and that said Letters Patent is hereby corrected as shown below:

On the title page item [56], should read

U.S. PATENT DOCUMENTS

| Document Number | Date | Name |
|---|---|---|
| 5,104,042 | 04/14/92 | McKown |
| 5,115,805 | 05/26/92 | Bommannan et al. |
| 5,163,433 | 11/17/92 | Kagawa et al. |
| 5,172,692 | 12/22/92 | Kulow et al. |
| 5,186,162 | 02/16/93 | Talish et al. |
| 5,197,946 | 03/30/93 | Tachibana |
| 5,211,160 | 05/18/93 | Talish et al. |
| 5,231,975 | 06/03/93 | Bommannan et al. |
| 5,269,291 | 12/14/93 | Carter |
| 5,315,998 | 05/31/94 | Tachibana et al. |
| 5,316,000 | 05/31/94 | Chapelon et al. |
| 5,318,014 | 06/07/94 | Carter |
| 5,323,769 | 06/28/94 | Bommannan et al. |
| 5,324,255 | 06/28/94 | Passafaro et al. |
| 5,345,940 | 09/13/94 | Seward et al. |
| 5,347,998 | 09/20/94 | Hodson et al. |
| 5,362,309 | 11/08/94 | Carter |

UNITED STATES PATENT AND TRADEMARK OFFICE
CERTIFICATE OF CORRECTION

PATENT NO. : 6,569,099 B1
APPLICATION NO. : 09/669312
DATED : May 27, 2003
INVENTOR(S) : Eilaz Babaev It is certified that error appears in the above-identified patent and that said Letters Patent is hereby corrected as shown below:

On the title page item [56], should read

FOREIGN PATENT DOCUMENTS

| | Document Number | Date | Country |
|---|---|---|---|
| WO | 96/35383 | 14/11/96 | WIPO |
| | | | |

OTHER DOCUMENTS

UNITED STATES PATENT AND TRADEMARK OFFICE
CERTIFICATE OF CORRECTION

PATENT NO. : 6,569,099 B1
APPLICATION NO. : 09/669312
DATED : May 27, 2003
INVENTOR(S) : Eilaz Babaev It is certified that error appears in the above-identified patent and that said Letters Patent is hereby corrected as shown below:

On the title page item [56], should read

U.S. PATENT DOCUMENTS

| Document Number | Date | Name |
|---|---|---|
| 5,374,266 | 12/20/94 | Kataoka et al. |
| 5,380,411 | 01/10/95 | Schlief |
| 5,393,296 | 02/28/95 | Rattner |
| 5,437,606 | 08/01/95 | Tsukamoto |
| 5,516,043 | 05/01/96 | Manna et al. |
| 5,520,166 | 05/28/96 | Ritson et al. |
| 5,520,612 | 05/08/96 | Winder et al. |
| 5,527,350 | 06/18/96 | Grove et al. |
| 5,529,572 | 06/25/96 | Spector |
| 5,545,124 | 08/13/96 | Krause et al. |
| 5,554,172 | 09/10/96 | Horner et al. |
| 5,556,372 | 09/17/96 | Talish et al. |
| 5,573,497 | 11/12/96 | Chapelon |
| 5,616,140 | 04/01/97 | Prescott |
| 5,626,554 | 05/06/97 | Ryaby et al. |
| 5,643,179 | 07/01/97 | Fujimoto |
| 5,656,016 | 08/12/97 | Ogden |

UNITED STATES PATENT AND TRADEMARK OFFICE
CERTIFICATE OF CORRECTION

PATENT NO. : 6,569,099 B1
APPLICATION NO. : 09/669312
DATED : May 27, 2003
INVENTOR(S) : Eilaz Babaev It is certified that error appears in the above-identified patent and that said Letters Patent is hereby corrected as shown below:

On the title page item [56], should read

U.S. PATENT DOCUMENTS

| Document Number | Date | Name |
|---|---|---|
| 5,658,323 | 08/19/97 | Miller |
| 5,699,805 | 12/23/97 | Seward et al. |
| 5,707,402 | 01/13/98 | Heim |
| 5,707,403 | 01/13/98 | Grove et al. |
| 5,735,811 | 04/07/98 | Brisken |
| 5,743,863 | 04/28/98 | Chapelon |
| 5,752,924 | 05/19/98 | Kaufman et al. |
| 5,762,616 | 06/09/98 | Talish |
| 5,730,705 | 03/24/98 | Talish et al. |
| 5,835,678 | 11/10/98 | Li et al. |
| 5,843,139 | 12/01/98 | Goedeke et al. |
| 5,879,314 | 03/09/99 | Peterson et al. |
| 5,879,364 | 03/09/99 | Bromfield et al. |
| 5,882,302 | 03/16/99 | Driscoll, Jr. et al. |
| 5,894,841 | 04/20/99 | Voges |
| 5,947,921 | 09/07/99 | Johnson et al. |
| 5,960,792 | 10/05/99 | Lloyd et al. |

UNITED STATES PATENT AND TRADEMARK OFFICE
CERTIFICATE OF CORRECTION

PATENT NO.       : 6,569,099 B1
APPLICATION NO.  : 09/669312
DATED            : May 27, 2003
INVENTOR(S)      : Eilaz Babaev It is certified that error appears in the above-identified patent and that said Letters Patent is hereby corrected as shown below:

On the title page item [56], should read

U.S. PATENT DOCUMENTS

| Document Number | Date | Name |
|---|---|---|
| 5,989,245 | 11/23/99 | Prescott |
| 6,001,069 | 12/14/99 | Tachibana et al. |
| 6,014,970 | 01/18/00 | Irvi et al. |
| 6,024,718 | 02/15/00 | Chen et al. |
| 6,026,808 | 02/22/00 | Armer et al. |
| 6,027,495 | 02/22/00 | Miller |
| 6,061,597 | 05/09/00 | Rieman et al. |
| 6,076,519 | 06/20/00 | Johnson |
| 6,083,159 | 07/04/00 | Driscoll, Jr. et al. |
| 6,095,141 | 08/01/00 | Armer et al. |
| 6,098,620 | 08/08/00 | Lloyd et al. |
| 6,102,298 | 08/15/00 | Bush et al. |
| 6,106,547 | 08/22/00 | Huei-Jung |
| 6,113,558 | 09/05/00 | Rosenschein et al. |
| 6,113,570 | 09/05/00 | Siegel et al. |
| 6,158,431 | 12/12/00 | Poole |
| 6,176,839 B1 | 01/23/01 | DeLuis et al. |

UNITED STATES PATENT AND TRADEMARK OFFICE
CERTIFICATE OF CORRECTION

PATENT NO.        : 6,569,099 B1
APPLICATION NO. : 09/669312
DATED             : May 27, 2003
INVENTOR(S)       : Eilaz Babaev It is certified that error appears in the above-identified patent and that said Letters Patent is hereby corrected as shown below:

On the title page item [56], should read

U.S. PATENT DOCUMENTS

| Document Number | Date | Name |
|---|---|---|
| 6,186,963 B1 | 02/13/01 | Schwarze et al. |
| 6,190,336 B1 | 02/20/01 | Duarte et al. |
| 6,206,842 B1 | 03/27/01 | Tu et al. |
| 6,206,843 B1 | 03/27/01 | Iger et al. |
| 6,231,528 B1 | 05/15/01 | Kaufman et al. |
| 6,273,864 B1 | 08/14/01 | Duarte et al. |
| 6,321,109 B2 | 11/20/01 | Ben-Haim et al. |
| 6,322,527 B1 | 11/27/01 | Talish |
| 6,325,769 B1 | 12/04/01 | Klopotek |

Signed and Sealed this

Twenty-third Day of June, 2009

JOHN DOLL
*Acting Director of the United States Patent and Trademark Office*

(12) EX PARTE REEXAMINATION CERTIFICATE (5995th)
United States Patent
Babaev

(10) Number: US 6,569,099 C1
(45) Certificate Issued: Nov. 6, 2007

(54) ULTRASONIC METHOD AND DEVICE FOR WOUND TREATMENT

(75) Inventor: Eilaz Babaev, Minnetonka, MN (US)

(73) Assignee: Celleration, Inc., Eden Prairie, MN (US)

Reexamination Request:
No. 90/007,613, Jul. 5, 2005

Reexamination Certificate for:
Patent No.: 6,569,099
Issued: May 27, 2003
Appl. No.: 09/669,312
Filed: Sep. 25, 2000

Certificate of Correction issued Sep. 23, 2003.

(51) Int. Cl.
*A61B 8/00* (2006.01)

(52) U.S. Cl. .............................. 600/439; 601/2; 601/3; 600/437; 604/22

(58) Field of Classification Search ................. 424/648; 600/439
See application file for complete search history.

(56) References Cited

U.S. PATENT DOCUMENTS

| | | |
|---|---|---|
| 3,275,059 A | 9/1966 | McCullough |
| 3,392,916 A | 7/1968 | Engstrom et al. |
| 3,522,801 A | 8/1970 | Robinson et al. |
| 3,860,173 A | 1/1975 | Sata |
| 3,874,372 A | 4/1975 | Le Bon |
| 4,052,004 A | 10/1977 | Martin et al. |
| 4,085,893 A | 4/1978 | Durley, III |
| 4,153,201 A | 5/1979 | Berger et al. |
| 4,251,031 A | 2/1981 | Martin et al. |
| 4,294,407 A | 10/1981 | Reichl et al. |
| 4,301,968 A | 11/1981 | Berger et al. |

(Continued)

FOREIGN PATENT DOCUMENTS

| | | |
|---|---|---|
| EP | 0 156 409 A2 | 2/1985 |
| EP | 0 437 155 B1 | 2/1990 |
| EP | 0416106 A1 | 3/1991 |
| EP | 0 657 226 B1 | 11/1994 |
| JP | 2000237275 A2 | 9/2000 |
| SU | 878268 | 11/1981 |
| SU | 1106485 A | 10/1982 |
| SU | 1827239 | 5/1990 |
| WO | WO 96/35383 | 11/1996 |
| WO | 97/17933 | 5/1997 |
| WO | 02/24150 A2 | 3/2002 |
| WO | 02/055131 A2 | 7/2002 |
| WO | 02/060525 A2 | 8/2002 |

OTHER PUBLICATIONS

"Comparison Possibilities of Ultrasound and Its Combination with Laser Surgery and Therapy", Zharov et al, pp. 331–339, In Biomedical Optoacoustics.
European Search Report dated Sep. 15, 2004.
International Search Report corresponding to PCT/US01/20096 (correspnding to U.S. Patent No. 6,559,099 B1).
XP–002290548, Abstract corresponding to SU 91 4099.
XP–004294507, Abstract corresponding to SU 188783D.
Journal of Burn Care & Rehabilitation; vol. 21, No. 4; Jul./Aug. 2000 pp. 333–338.
Design and Application of Low–Frequency Ultrasound and Its Combination With Laser Radiation in Surgery and Therapy—Critical Reviews in Biomedical Engineering; 2001; pp. 502–519.

*Primary Examiner*—Beverly M. Flanagan

(57) ABSTRACT

The method and device of the present invention for wound treatment includes a transducer to produce waves, preferably ultrasonic waves. The transducer has tip with the distal end (radiation surface). A liquid is directed to the radiation surface wherein an directed atomized particle spray of the liquid is created upon contact of the liquid with the radiation surface. The spray directed to the wound from at least 0.1 inches transmits wave trough particles and has an irrigation, m

U.S. PATENT DOCUMENTS

| | | | |
|---|---|---|---|
| 4,331,137 A | | 5/1982 | Sarui |
| 4,352,459 A | | 10/1982 | Berger et al. |
| 4,414,202 A | * | 11/1983 | Silvetti ................ 424/648 |
| 4,428,531 A | | 1/1984 | Martin |
| 4,466,571 A | | 8/1984 | Muhlbauer |
| 4,530,360 A | | 7/1985 | Duarte |
| 4,541,564 A | | 9/1985 | Berger et al. |
| 4,551,139 A | | 11/1985 | Plaas et al. |
| 4,619,400 A | | 10/1986 | Van Der Burgt |
| 4,642,581 A | | 2/1987 | Erickson |
| 4,655,393 A | | 4/1987 | Berger |
| 4,659,014 A | | 4/1987 | Soth et al. |
| 4,679,551 A | | 7/1987 | Anthony |
| 4,726,523 A | | 2/1988 | Kokubo et al. |
| 4,726,525 A | | 2/1988 | Yonekawa et al. |
| 4,733,820 A | | 3/1988 | Endo et al. |
| 4,756,478 A | | 7/1988 | Endo et al. |
| 4,783,003 A | | 11/1988 | Hirabayashi et al. |
| 4,790,479 A | | 12/1988 | Matsumoto et al. |
| 4,815,661 A | | 3/1989 | Anthony |
| 4,850,534 A | | 7/1989 | Takahashi et al. |
| 4,905,671 A | | 3/1990 | Senge et al. |
| 4,930,700 A | | 6/1990 | McKown |
| 4,941,618 A | | 7/1990 | Hildebrand et al. |
| 4,961,885 A | | 10/1990 | Avrahami et al. |
| 4,982,730 A | | 1/1991 | Lewis, Jr. |
| 5,002,059 A | | 3/1991 | Crowley et al. |
| 5,040,537 A | | 8/1991 | Katakura |
| 5,062,795 A | | 11/1991 | Woog |
| 5,063,922 A | | 11/1991 | Hakkinen |
| 5,076,266 A | | 12/1991 | Babaev |
| 5,104,042 A | | 4/1992 | McKown |
| 5,115,805 A | | 5/1992 | Bommannan et al. |
| 5,163,433 A | | 11/1992 | Kagawa et al. |
| 5,171,215 A | | 12/1992 | Flanagan |
| 5,172,692 A | | 12/1992 | Kulow et al. |
| 5,186,162 A | | 2/1993 | Talish et al. |
| 5,197,946 A | | 3/1993 | Tachibana |
| 5,211,160 A | | 5/1993 | Talish et al. |
| 5,231,975 A | | 8/1993 | Bommannan et al. |
| 5,269,291 A | | 12/1993 | Carter |
| 5,315,998 A | | 5/1994 | Tachibana et al. |
| 5,316,000 A | | 5/1994 | Chapelon et al. |
| 5,318,014 A | | 6/1994 | Carter |
| 5,323,769 A | | 6/1994 | Bommannan et al. |
| 5,324,255 A | | 6/1994 | Passafaro et al. |
| 5,345,940 A | | 9/1994 | Seward et al. |
| 5,347,998 A | | 9/1994 | Hodson et al. |
| 5,362,309 A | | 11/1994 | Carter |
| 5,374,266 A | | 12/1994 | Kataoka et al. |
| 5,380,411 A | | 1/1995 | Schlief |
| 5,393,296 A | | 2/1995 | Rattner |
| 5,437,606 A | | 8/1995 | Tsukamoto |
| 5,516,043 A | | 5/1996 | Manna et al. |
| 5,520,166 A | | 5/1996 | Ritson et al. |
| 5,520,612 A | | 5/1996 | Winder et al. |
| 5,527,350 A | | 6/1996 | Grove et al. |
| 5,529,572 A | | 6/1996 | Spector |
| 5,545,124 A | | 8/1996 | Krause et al. |
| 5,554,172 A | | 9/1996 | Horner et al. |
| 5,556,372 A | | 9/1996 | Talish et al. |
| 5,573,497 A | | 11/1996 | Chapelon |
| 5,616,140 A | | 4/1997 | Prescott |
| 5,626,554 A | | 5/1997 | Ryaby et al. |
| 5,643,179 A | | 7/1997 | Fujimoto |
| 5,656,016 A | | 8/1997 | Ogden |
| 5,658,323 A | | 8/1997 | Miller |
| 5,688,224 A | * | 11/1997 | Forkey et al. ............... 600/200 |
| 5,699,805 A | | 12/1997 | Seward et al. |
| 5,702,360 A | | 12/1997 | Dieras et al. |
| 5,707,402 A | | 1/1998 | Heim |
| 5,707,403 A | | 1/1998 | Grove et al. |
| 5,730,705 A | | 3/1998 | Talish et al. |
| 5,735,811 A | | 4/1998 | Brisken |
| 5,743,863 A | | 4/1998 | Chapelon |
| 5,752,924 A | * | 5/1998 | Kaufman et al. ............... 601/2 |
| 5,762,616 A | | 6/1998 | Talish |
| 5,835,678 A | | 11/1998 | Li et al. |
| 5,843,139 A | | 12/1998 | Goedeke et al. |
| 5,879,314 A | | 3/1999 | Peterson et al. |
| 5,879,364 A | | 3/1999 | Bromfield et al. |
| 5,882,302 A | | 3/1999 | Driscoll, Jr. et al. |
| 5,894,841 A | | 4/1999 | Voges |
| 5,947,921 A | | 9/1999 | Johnson et al. |
| 5,960,792 A | | 10/1999 | Lloyd et al. |
| 5,989,245 A | | 11/1999 | Prescott |
| 6,001,069 A | | 12/1999 | Tachibana et al. |
| 6,014,970 A | | 1/2000 | Irvi et al. |
| 6,024,718 A | | 2/2000 | Chen et al. |
| 6,026,808 A | | 2/2000 | Armer et al. |
| 6,027,495 A | | 2/2000 | Miller |
| 6,061,597 A | | 5/2000 | Rieman et al. |
| 6,076,519 A | | 6/2000 | Johnson |
| 6,083,159 A | | 7/2000 | Driscoll, Jr. et al. |
| 6,095,141 A | | 8/2000 | Armer et al. |
| 6,098,620 A | | 8/2000 | Lloyd et al. |
| 6,102,298 A | | 8/2000 | Bush et al. |
| 6,106,547 A | | 8/2000 | Huei-Jung |
| 6,113,558 A | | 9/2000 | Rosenschein et al. |
| 6,113,570 A | | 9/2000 | Siegel et al. |
| 6,139,320 A | | 10/2000 | Hahn |
| 6,158,431 A | | 12/2000 | Poole |
| 6,161,536 A | * | 12/2000 | Redmon et al. ....... 128/200.14 |
| 6,176,839 B1 | | 1/2001 | DeLuis et al. |
| 6,186,963 B1 | | 2/2001 | Schwarze et al. |
| 6,190,336 B1 | | 2/2001 | Duarte et al. |
| 6,206,842 B1 | | 3/2001 | Tu et al. |
| 6,206,843 B1 | | 3/2001 | Iger et al. |
| 6,231,528 B1 | | 5/2001 | Kaufman et al. |
| 6,273,864 B1 | | 8/2001 | Duarte et al. |
| 6,321,109 B2 | | 11/2001 | Ben-Haim et al. |
| 6,322,527 B1 | | 11/2001 | Talish |
| 6,325,769 B1 | | 12/2001 | Klopotek |
| 2002/0062093 A1 | | 5/2002 | Soring et al. |
| 2003/0023193 A1 | | 1/2003 | Soring et al. |

* cited by examiner

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 5, 8–15, 19 and 20 are cancelled.

Claims 1 and 16 are determined to be patentable as amended.

Claims 2–4, 6, 7, 17 and 18, dependent on an amended claim, are determined to be patentable.

New claim 21 is added and determined to be patentable.

1. A method for treating a wound comprising the steps of:
providing a transducer having a distal radiation surface arranged a distance from the surface of the wound for emitting ultrasonic energy;
introducing [at least one of] a liquid [and a powder] *consisting essentially of a saline solution, which saline solution does not include a medicament,* to the distal radiation surface to produce a spray *of said saline solution*; and
delivering the emitted ultrasonic energy to the wound through the spray, wherein the ultrasonic energy penetrates the wound tissue to a beneficial depth to provide a bactericidal and a therapeutic effect for decreasing the healing time for the wound.

16. A method for treating a wound comprising the steps of:
generating ultrasonic energy at a distance from the surface of the wound, such that the generated ultrasonic energy propagates through a gaseous medium;
introducing [at least one of] a liquid [and a powder] *consisting essentially of a saline solution, which saline solution does not include a medicament,* in at least one propagation path of the generated ultrasonic energy to produce a spray *of said saline solution*; and
delivering the generated ultrasonic energy to the wound through the spray, wherein the ultrasonic energy penetrates the wound tissue to a beneficial depth to provide a bactericidal and a therapeutic effect for decreasing the healing time for the wound.

*21. The method according to claim 1, wherein the transducer includes a disposable nozzle that allows delivery of the liquid to a lateral surface of a transducer tip or directly to a radiation surface of the transducer.*

\* \* \* \* \*